United States Patent [19]
Suzanne et al.

[11] Patent Number: 5,251,005
[45] Date of Patent: Oct. 5, 1993

[54] BURNER USABLE IN AN APPARATUS FOR ANALYZING A GAS COMPOSITION BY FLAME SPECTROPHOTOMETRY

[75] Inventors: Pierre Suzanne, Oncy sur Ecole; Patrick Bleuse, Le Quesnoy; Gilles Guene, Elancourt; Pierre Clausin, Ville d'Avray, all of France

[73] Assignees: L'etat Francais, represente par le Delegue General pour l'Armement; Proengin S.A., both of France

[21] Appl. No.: 628,542

[22] Filed: Dec. 17, 1990

[30] Foreign Application Priority Data
Dec. 18, 1989 [FR] France .................. 89 16876

[51] Int. Cl.5 ........................... G01N 21/72
[52] U.S. Cl. ................................ 356/315
[58] Field of Search ................. 356/315, 417

[56] References Cited
U.S. PATENT DOCUMENTS
3,580,680 5/1971 Crider ...................... 356/315

Primary Examiner—Vincent P. McGraw
Assistant Examiner—K. P. Hantis
Attorney, Agent, or Firm—William A. Drucker

[57] ABSTRACT

A burner is disclosed which can be used in an apparatus for analyzing a gas composition by flame spectrophotometry, comprising, disposed coaxially with each other, a tubular body having an open end on which an optical system is mounted coaxially, a sample taking nozzle which extends the body while defining an intake chamber, a collar fast with the body through which passes a tubular chimney, a nozzle for intake of the gas composition which is fitted in the chimney while forming therewith an annular intercalary chamber into which opens a fuel gas intake duct and a capillary tube for intake of the gas composition to be analyzed, this capillary tube being connected to the intake duct at the level of its end situated in the intake chamber.

11 Claims, 2 Drawing Sheets

BURNER USABLE IN AN APPARATUS FOR ANALYZING A GAS COMPOSITION BY FLAME SPECTROPHOTOMETRY

BACKGROUND OF THE INVENTION

1. Field of the Invention

The present invention relates to a burner usable in an apparatus for the analysis of a gas composition by flame spectrophotometry, said gas composition possibly comprising a mixture of gases with possibly particles or vesicles in suspension.

This process consists in carrying out a spectrophotographic analysis of the radiation produced by the flame of a gas mixture including the elements to be analyzed. This analysis may be carried out by isolating the characteristic radiations of the elements sought and measuring the intensity of these radiations by photometric means.

In the case of analysis of the ambient air, the flame is usually obtained by combustion, inside the burner, of a constant flow hydrogen stream in the air flow to be analyzed.

The purpose of the invention is particularly, but not exclusively, to provide a burner of this kind which can be used in a portable apparatus for instantaneously measuring with direct reading the gas element content in the ambient air.

2. Description of the Prior Art

Of course, apparatus of this kind, one of which is described in the patent FR 87 02762 in the name of the firm PROENGIN S.A., must have dimensions as small as possible, so as to be readily carried by hand and handled in the field.

Furthermore, they must be designed so as to be able to be used in media whose parameters may vary considerably, whether it is a question of the temperature ($-32°$ C. to $+55°$ C.), of the humidity, the purity of the air (proportion of particles in suspension), the contaminating power of the substances contained in the element sought, etc. . . . .

Furthermore, such apparatus must have a response time which is as short as possible (not only between the moment marking the beginning of sample taking and the moment when the proportion of the element sought is indicated, but again between the end of sample taking and the moment when the initial conditions are reestablished).

At the present time, none of the apparatus commercially available satisfies all these requirements.

The aim of the invention is more particularly to fill in this gap.

SUMMARY OF THE INVENTION

For this it provides a burner specially designed so as to make possible the construction of an apparatus answering the above mentioned main criteria, for the reasons which will be explained hereafter.

According to the invention, this burner comprises more precisely, disposed coaxially with respect to each other:

- a tubular body preferably made from a heat insulating material, this body having an open end on which the optical system associated with the burner is fitted coaxially;
- a sample taking nozzle which extends said body from its second end while defining an intake chamber open outwardly;
- a tubular skirt solid with the body and forming therewith at least one axial channel (demisting channel) opening on one side, in the vicinity of the optical system and communicating on the other side with the intake chamber through a calibrated orifice, and a suction chamber situated preferably in a region opposite said channel and opening in the vicinity of the optical system, this chamber being connected to suction means through a lateral orifice provided in the body;
- a radial collar fast with the body and/or with the skirt, through which passes a tubular chimney which extends coaxially in the body, over a part of its length, this collar forming a calibrated heat conduction bridge between said body and said chimney;
- a nozzle for the intake of the gas composition which extends inside the intake chamber, to be fitted partially in the chimney while forming therewith an annular intercalary chamber closed on one side and which opens on the other side into the inner volume of the chimney, at the level of a combustion chamber, this annular chamber being connected to a constant flow fuel gas source through an intake duct;
- a capillary tube for intake of the gas composition to be analyzed, connected to the intake nozzle, at the level of its end situated in the intake chamber, this capillary tube being preferably bent so as to prevent the transmission of ambient light to the combustion chamber.

BRIEF DESCRIPTION OF THE DRAWINGS

The features of the above defined burner will be clear from the following description of one embodiment of the invention illustrated by the accompanying drawings in which.

DESCRIPTION OF THE PREFERRED EMBODIMENT

Figure 2:
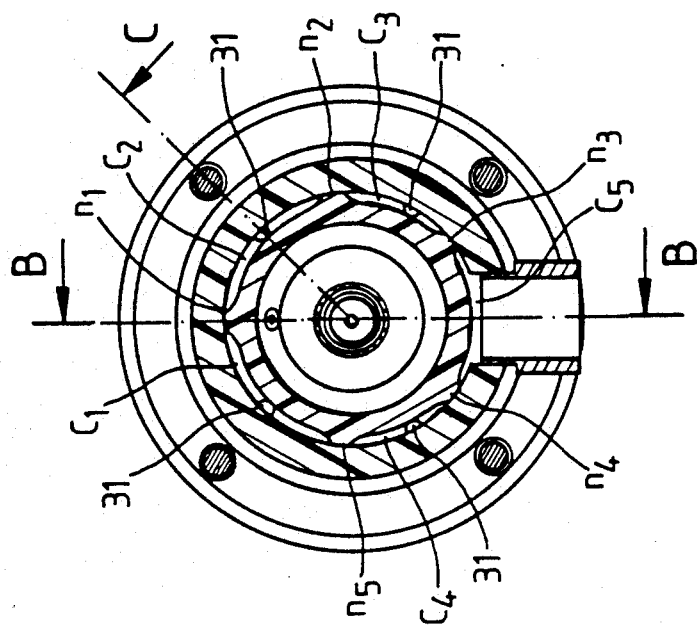
FIG. 2 is a cross section through AA of FIG. 1.
Figure 1:
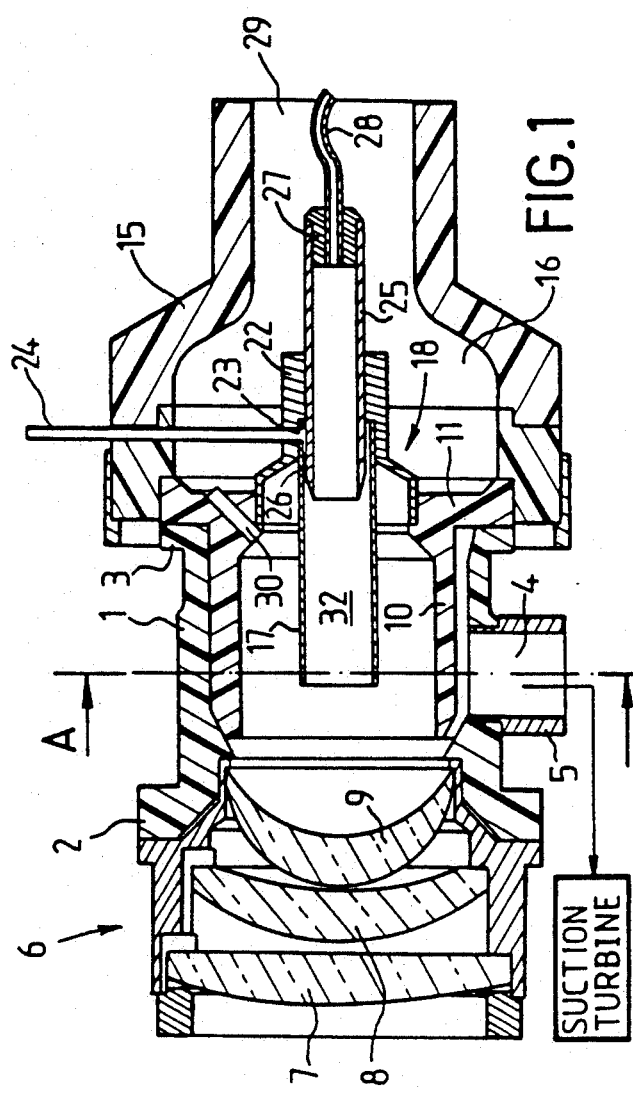
FIG. 1 is an axial section (through BB of FIG. 2) of a burner according to the invention for analyzing the ambient air and using hydrogen as fuel gas.
Figure 3:
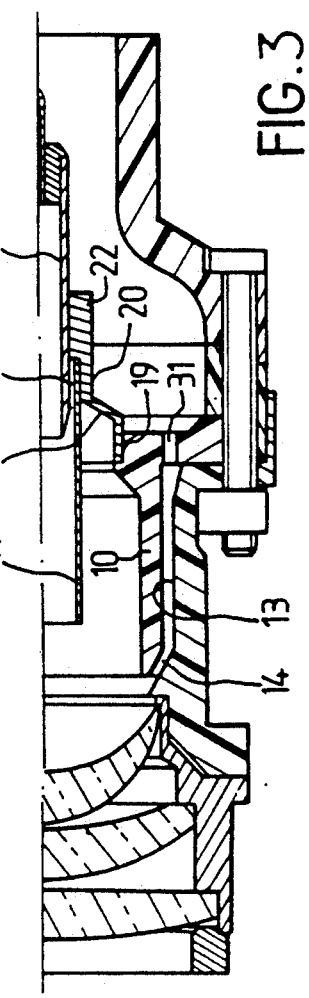
FIG. 3 is a half axial section in the plane C of FIG. 2.

Such as shown in the drawings, the burner comprises first of all a body 1 consisting of a substantially cylindrical tubular section whose ends 2, 3 are edged with two radially projecting circular flanges and whose cylindrical wall has an orifice 4 with a radial connector 5 for connection to a suction turbine, for example by means of a flexible tube. Advantageously, body 1 will be made from a heat insulating plastic material also heat resistant (for example to a temperature of 260° C. to 300° C.). Such a plastic material may be found in the market under the trademarks "Torlon" or "Vespel".

To one end 2 is fixed an optical system 6 formed of three lenses 7, 8, 9, coaxial with body 1 and the focal point of which is situated at a given position on the axis of this body 1.

Inside body 1 is fitted a tubular skirt 10 of cylindrical shape made from the same material as the body and ending on one side in a collar 11 which is sealingly applied against the flange equipping the end 3 of body 1. In this example, the external surface of skirt 10 which extends parallel to and at a short distance from the internal wall 13 of body 1 has five axial ribs $n_1$ to $n_5$ projecting radially, in sealing contact with the internal wall 13.

These axial ribs $n_1$ to $n_5$ define then five axial channels, four of which $C_1$ to $C_4$ form demisting channels whose role will be defined hereafter and a fifth channel $C_5$ which communicates with orifice 4 and which serves then as suction chamber.

Channels $C_1$ to $C_5$ are closed on one side by collar 11 and on the other side open through a slightly oblique surface 14 oriented substantially tangentially to the concave face of lens 9 and in the vicinity thereof.

On the assembly comprising the flange formed by end 3 of body 1 and collar 11 is fitted, by its largest diameter end, a sample taking nozzle 15 in the form of a funnel which extends body 1 coaxially while defining an intake chamber 16. This nozzle 15 may advantageously be made from a plastomer of polytetrafluoroethylene type (PTFE, FEP) or similar.

Inside the inner volume defined by skirt 10 is coaxially disposed a chimney 17, of cylindrical shape, fixed by its end opposite the optical system 6 to the base of collar 11, by means of a tubular connecting piece 18 comprising:
- a first cylindrical sleeve 19 fast with collar 11;
- a second cylindrical sleeve 20 of smaller diameter in which chimney 17 is fitted;
- a tapered portion 21 connecting the first and second sleeves 19, 20 together; and
- a third cylindrical sleeve 22 which extends the second sleeve 20 and has an inner diameter slightly less that that of the latter.

Chimney 17 and sleeve 20 have, in the zone where they are fitted together, a through orifice 23 connected to a radial capillary tube 24 which passes through the sample taking nozzle 15, so as to be connected to a hydrogen intake tube connected to a constant flow hydrogen generator.

In the third cylindrical sleeve 22 is fitted an intake nozzle 25 which is engaged inside chimney 17, over a fraction thereof, while forming an intercalary annular chamber 26 into which the hydrogen intake orifice 23 opens. This nozzle 25 further extends inside the intake chamber 16 and ends therein by an end closed by a plug 27 through which passes a bent capillary tube 28 opening to the outside substantially at the level of orifice 29 of the sample taking nozzle 15.

Calibrated passages 30, 31 formed in collar 11 of skirt 10 are provided so as to place the intake chamber 16 respectively in communication with the demisting channels $C_1$ to $C_4$ and the volume included between chimney 17 and skirt 10.

The operation of the above described burner is then the following:

Start-up of the turbine generates inside body 1 a depression which results in the suction of air through the demisting channels $C_1$ to $C_4$, through the ignition channel 30 and through the air intake capillary tube 28.

At the same time, start-up of the hydrogen generator causes hydrogen to be injected with a constant flow into the intercalary volume 26.

The air flow and hydrogen flow respectively from the intake nozzle 25 and the intercalary volume 26 are intimately mixed inside the combustion chamber 32 formed by chimney 17. The air analysis and hydrogen flow rates are adjusted so as to obtain in the combustion chamber 32 a gas mixture in which the hydrogen is in excess.

Ignition of this mixture is obtained by means of a spark igniter or even an incandescent wire igniter acting in a zone situated slightly beyond chimney 17, on the axis of symmetry of body 1. The air stream from the ignition channel 30 then causes in this zone a gas mixture in which the air is in excess and which is consequently favorable for ignition.

Once ignited, the flame is stabilized in the combustion chamber 32 and so inside chimney 17, at a position set back from the focal point of the optical system.

Of course, such combustion generates intense heating of chimney 17 which consequently is made from an appropriate metal alloy such as "Inconel".

To overcome a certain number of problems, such as the formation of mist on the concave surface of lens 9, frosting up of the discharge orifice 4 when the apparatus is used in a medium at very low temperature, contamination of the capillary tube 28 and of the nozzle 25 for intake of the gas to be analyzed, by the material in suspension containing the element sought, the inner portion or core of the burner and, in particular, nozzle 25, chimney 17 and capillary tube 28 must be as hot as possible.

For this, the thickness of body 1, skirt 10 and of the sample taking nozzle 15 is relatively large so that the heat losses are minimum because of the low heat conductivity of the plastic material used.

Furthermore, the tapered portion 21 of the tubular connecting piece 18 has a thickness as small as possible so as to reduce as much as possible the heat conduction bridge between chimney 17 and body 1.

Furthermore, plug 27 which closes nozzle 25 is made from a good heat conducting material for heating the capillary tube 28. This latter will of course be made from a good heat conducting material or be covered with a good heat conducting coating.

With such arrangements, the contaminatable elements of the burner are brought to a sufficient temperature to dissociate and/or evaporate the contaminating materials which might possibly be deposited there and which would otherwise risk vitiating the measurements.

Furthermore, the air flow inside the burner is sufficiently heated to eliminate any risk of frosting due to the high water content of the gas following combustion.

Because it is isolated from the combustion gas by the air flows from the demisting channels $C_1$ to $C_4$, lens 9 will not be subject to water vapor deposits.

The risk of disturbance of the measurements by the parasite light is overcome through the bend in the capillary tube 28 which forms a baffle preventing light from passing. Furthermore, parasite reflections may be overcome by adopting a black color for the main parts of the burner and, in particular, body 1 and the sample taking nozzle 15.

Of course, the invention is not limited to the above described embodiments.

Figure 4:
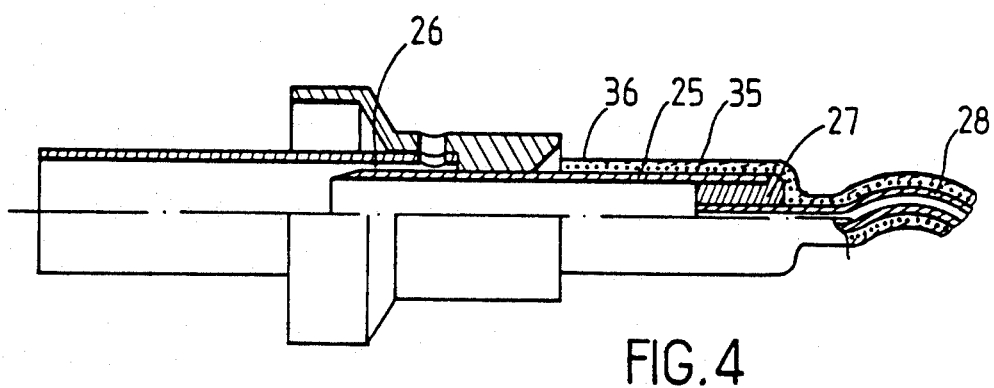
FIGS. 4, 5 and 6 are views, partially in axial section, of three respective variants of the core of the burner including the chimney, the intake nozzle and the capillary tube for intake of the gas composition to be analyzed.

Thus, for example, the capillary tube 28 of bent shape could be covered as well as the nozzle portion 25 situated in the intake chamber 15 by a winding 35 made from a good heat conducting metal wire, such as copper, this winding carrying a coating 36 for example of resin (FIG. 4).

Figure 5:
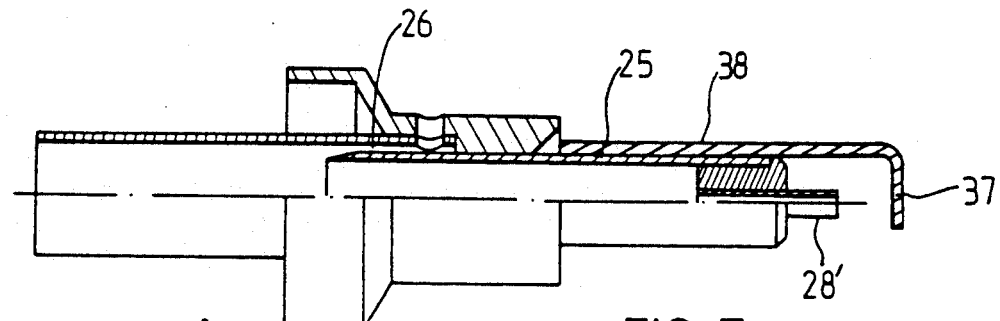
Figure 6:
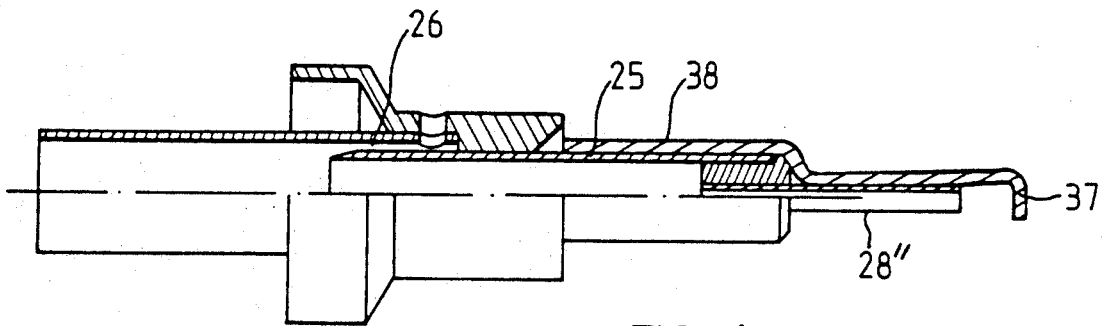

In another embodiment, the capillary tube 28' extends coaxially to nozzle 25 and is relatively short. In this case, the propagation of the ambient light inside capillary tube 28' as well as its protection against dust may be provided by a deflector 37 masking the orifice of the capillary tube 28' and carried by an axial support 38 fast with nozzle 25 (FIG. 5). In the case of a straight nozzle of greater length 28", the axial support 38 may be made from a good heat conducting material enveloping said nozzle 25 and said capillary tube 28" at least partially (FIG. 6).

An important advantage of the above described structure resides in the original combination of the intake circuits for the hydrogen and the gas to be analyzed which open axially into a coaxial combustion chamber 32, the gas intake circuit being reduced to its simplest form. With this combination the burner reaches its optimum operating conditions very rapidly and thus very short response times are obtained. Furthermore, because the inner volume of the body communicates with the outside only through intake circuits formed by capillary tubes generating high head losses, the disturbances caused by the wind are eliminated.

What is claimed is:

1. A burner usable in an apparatus for analyzing a gas composition by flame spectrometry, comprising, disposed coaxially with respect to each other
   i. a tubular body having a first open end portion provided with a coaxial optical system and a second open end portion located opposite said first end portion, said body delimiting an internal chamber;
   ii. a sample taking nozzle which extends said body from said second end portion while defining an intake chamber provided with an intake orifice;
   iii. a tubular skirt mounted coaxially in said internal chamber and forming with said body at least one intercalary demisting channel opening on one side in the vicinity of said optical system and communicating on the other side with said intake chamber through a calibrated orifice, and a suction chamber which communicates with said internal chamber through a suction opening located in the vicinity of the optical system and with external suction means through a lateral orifice provided in said body;
   iv. a radial collar extending radially from said second end portion of said body and provided with a coaxial bore, through which is sealingly engaged a coaxial tubular chimney extending in said internal chamber over a part of its length and separating said intake chamber from a combustion chamber which opens in front of said optical system;
   v. an intake nozzle for said gas composition which extends inside said intake chamber and which is partially engaged coaxially inside said chimney, while forming therewith an annular intercalary chamber which communicates with said combustion chamber, said annular intercalary chamber being connected to a constant flow combustible gas source through an intake duct; and
   vi. a capillary tube for intake of said gas composition, said capillary tube being connected to said intake nozzle by an end located in said intake chamber.

2. The burner as claimed in claim 1, wherein said body, said tubular skirt and said sample taking nozzle are made from a heat insulating material.

3. The burner as claimed in claim 1, wherein said radial collar is adapted so as to have high heat resistance between said body and/or said skirt and said chimney.

4. The burner as claimed in claim 1, wherein said intercalary demisting channel comprises an outlet oriented obliquely towards said optical system.

5. The burner as claimed in claim 1, comprising ignition means situated in the vicinity of said combustion chamber and wherein said skirt delimites with said chimney an ignition chamber which communicates with said intake chamber through a calibrated ignition channel.

6. The burner as claimed in claim 1, comprising means for preventing passage of parasite light rays through said capillary tube.

7. The burner as claimed in claim 6, wherein said prevention means are formed by a bend in said capillary tube.

8. The burner as claimed in claim 6, wherein said prevention means consist of a deflector disposed in line with an external orifice of said capillary tube.

9. The burner as claimed in claim 1, further comprising means for promoting heat transfers between said intake nozzle and said capillary tube.

10. The burner as claimed in claim 9, wherein said heat transfer means consist of a winding made from a good heat conducting material wire, possibly covered with a coating.

11. The burner as claimed in claim 9, wherein said heat transfer means consist of an axial element made from a good heat conducting material which envelopes said nozzle and said capillary tube at least partially and which possibly serves as a support for a deflector situated opposite the orifice of said capillary tube.

* * * * *